(12) United States Patent
Fort et al.

(10) Patent No.: US 7,364,752 B1
(45) Date of Patent: Apr. 29, 2008

(54) SOLID DISPERSION PHARAMACEUTICAL FORMULATIONS

(75) Inventors: James J. Fort, Midlothian, VA (US); Steven L. Krill, Chatham, NJ (US); Devalina Law, Libertyville, IL (US); Yihong Qiu, Gurnee, IL (US); William R. Porter, Vernon Hills, IL (US); Eric A. Schmitt, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 688 days.

(21) Appl. No.: 09/709,829

(22) Filed: Nov. 10, 2000

Related U.S. Application Data

(60) Provisional application No. 60/165,018, filed on Nov. 12, 1999.

(51) Int. Cl.
*A61K 8/72* (2006.01)
*A61K 9/20* (2006.01)
*A61K 9/48* (2006.01)
*A61K 31/425* (2006.01)
*A61K 31/505* (2006.01)

(52) U.S. Cl. ............... 424/455; 424/464; 424/484; 424/486; 514/274; 514/365; 514/772; 514/772.3; 514/937

(58) Field of Classification Search ............... 424/455, 424/464, 484, 486; 514/274, 365, 772, 772.3, 514/937
See application file for complete search history.

(56) References Cited

U.S. PATENT DOCUMENTS

| | | |
|---|---|---|
| 4,758,427 A | 7/1988 | Leeson |
| 4,769,235 A | 9/1988 | Penoz et al. |
| 4,769,236 A | 9/1988 | Panoz et al. |
| 4,801,460 A | 1/1989 | Goertz et al. |
| 4,851,438 A | 7/1989 | Flashinski |
| 4,880,585 A | 11/1989 | Klimesch et al. |
| 4,904,699 A | 2/1990 | Bauer |
| 4,957,681 A | 9/1990 | Klimesch et al. |
| 4,996,058 A | 2/1991 | Sinnreich |
| 5,073,379 A | 12/1991 | Klimesch et al. |
| 5,145,683 A | 9/1992 | Rhodes |
| 5,405,616 A | 4/1995 | Wunderlich et al. |
| 5,456,923 A | 10/1995 | Nakamichi et al. |
| 5,490,990 A | 2/1996 | Grabowski et al. |

(Continued)

FOREIGN PATENT DOCUMENTS

CA 2 343 234 3/2000

(Continued)

OTHER PUBLICATIONS

W. L. Chiou, et al., "Pharmaceutical Applications of Solid Dispersion System", Journal of Pharmaceutical Sciences, 60 (9), (1971), 1281-1302.

(Continued)

*Primary Examiner*—Jeffrey Edwin Russel

(57) ABSTRACT

A pharmaceutical composition is disclosed which comprises a solid dispersion of an HIV protease inhibitor in a water soluble carrier, such as PEG, having enhanced bioavailability and improved dissolution properties. The solid dispersion may optionally be encapsulated in hard gelatin capsules, compressed into a tablet, or may be granulated with a pharmaceutically acceptable granulating agent. Also disclosed are methods of making said solid dispersion and methods of treating an HIV infection employing said solid dispersion.

10 Claims, 5 Drawing Sheets

U.S. PATENT DOCUMENTS

| | | | |
|---|---|---|---|
| 5,525,628 A | 6/1996 | Nicola et al. | |
| 5,541,206 A | 7/1996 | Kempf et al. | |
| 5,545,628 A | 8/1996 | Deboeck et al. | |
| 5,552,159 A | 9/1996 | Mueller et al. | |
| 5,559,158 A | 9/1996 | Al-Razzak et al. | |
| 5,610,193 A * | 3/1997 | Al-Razzak et al. | 514/616 |
| 5,641,516 A | 6/1997 | Grabowski et al. | |
| 5,648,497 A | 7/1997 | Kempf et al. | |
| 5,725,878 A | 3/1998 | Al-Razzak et al. | |
| 5,727,878 A | 3/1998 | Al-Razzak et al. | |
| 5,741,519 A | 4/1998 | Rosenberg et al. | |
| 5,773,025 A | 6/1998 | Baichwal | |
| 5,889,051 A | 3/1999 | Chen et al. | 514/530 |
| 5,897,910 A | 4/1999 | Rosenberg et al. | |
| 5,914,332 A * | 6/1999 | Sham et al. | 514/274 |
| 5,939,099 A | 8/1999 | Grabowski et al. | |
| 5,945,123 A | 8/1999 | Hermelin | |
| 5,945,127 A | 8/1999 | Breitenbach et al. | |
| 5,948,426 A | 9/1999 | Al-Razzak et al. | |
| 5,948,436 A | 9/1999 | Al-Razzak et al. | |
| 5,969,181 A | 10/1999 | Breitenbach et al. | |
| 6,001,391 A | 12/1999 | Zeidler et al. | |
| 6,009,690 A | 1/2000 | Rosenberg et al. | |
| 6,027,747 A | 2/2000 | Terracol et al. | |
| 6,037,157 A | 3/2000 | Norbeck et al. | |
| 6,063,821 A | 5/2000 | Breitenbach et al. | |
| 6,066,334 A | 5/2000 | Kolter et al. | |
| 6,083,518 A | 7/2000 | Lindahl | |
| 6,120,802 A | 9/2000 | Breitenbach et al. | |
| 6,132,659 A | 10/2000 | Rosenberg et al. | |
| 6,150,424 A | 11/2000 | Breitenbach et al. | |
| 6,187,342 B1 | 2/2001 | Zeidler et al. | |
| 6,197,781 B1 | 3/2001 | Guitard et al. | |
| 6,197,787 B1 * | 3/2001 | Franson et al. | 514/313 |
| 6,221,368 B1 | 4/2001 | Breitenbach et al. | |
| 6,248,363 B1 | 6/2001 | Patel et al. | |
| 6,251,434 B1 | 6/2001 | Breitenbach et al. | |
| 6,281,282 B1 | 8/2001 | Breitenbach et al. | |
| 6,290,990 B1 | 9/2001 | Grabowski et al. | |
| 6,294,192 B1 | 9/2001 | Patel et al. | |
| 6,318,650 B1 | 11/2001 | Breitenbach et al. | |
| 6,322,816 B1 | 11/2001 | Zeidler et al. | |
| 6,350,398 B1 | 2/2002 | Breitenbach et al. | |
| 6,383,471 B1 | 5/2002 | Chen et al. | |
| 6,387,401 B2 | 5/2002 | Rosenberg et al. | |
| 6,423,256 B1 | 7/2002 | Kothrade et al. | |
| 6,436,440 B1 | 8/2002 | Meffert et al. | |
| 6,451,339 B2 | 9/2002 | Patel et al. | |
| 6,462,093 B1 | 10/2002 | Miyamoto et al. | |
| 6,465,011 B2 | 10/2002 | Law et al. | |
| 6,488,939 B1 | 12/2002 | Zeidler et al. | |
| 6,547,997 B1 | 4/2003 | Breitenbach et al. | |
| 6,599,528 B1 | 7/2003 | Rosenberg et al. | |
| 6,599,931 B1 | 7/2003 | Breitenbach et al. | |
| 6,608,198 B2 | 8/2003 | Dickman et al. | |
| 6,669,879 B1 | 12/2003 | Spengler et al. | |
| 6,669,883 B1 | 12/2003 | Rosenberg et al. | |
| 6,692,767 B2 | 2/2004 | Burnside et al. | |
| 6,730,319 B2 | 5/2004 | Maeder et al. | |
| 6,733,781 B2 | 5/2004 | Abu-Izza et al. | |
| 6,737,005 B1 | 5/2004 | Rosenberg et al. | |
| 6,787,157 B1 | 9/2004 | Rosenberg et al. | |
| 6,834,310 B2 | 12/2004 | Munger et al. | |
| 6,894,171 B1 | 5/2005 | Bauer et al. | |
| 7,014,810 B2 | 3/2006 | Krull et al. | |
| 7,148,359 B2 | 12/2006 | Chemburkar et al. | |
| 7,229,641 B2 | 6/2007 | Cherukuri | |
| 2001/0006650 A1 | 7/2001 | Burnside et al. | |
| 2002/0006443 A1 | 1/2002 | Curatolo et al. | |
| 2002/0114833 A1 | 8/2002 | Abu-Izza et al. | |
| 2002/0161884 A1 | 10/2002 | Munger et al. | |
| 2002/0187188 A1 | 12/2002 | Cherukuri | |
| 2003/0015814 A1 | 1/2003 | Kurll et al. | |
| 2003/0039686 A1 | 2/2003 | Maeder et al. | |
| 2003/0054038 A1 | 3/2003 | Crew et al. | |
| 2003/0072801 A1 | 4/2003 | Curatolo et al. | |
| 2003/0091630 A1 | 5/2003 | Louie-Helm et al. | |
| 2003/0091643 A1 | 5/2003 | Friesen et al. | |
| 2003/0096791 A1 | 5/2003 | Gupte et al. | |
| 2003/0104063 A1 | 6/2003 | Babcock et al. | |
| 2003/0153608 A1 | 8/2003 | Maegerlein et al. | |
| 2003/0161884 A1 | 8/2003 | Rosenberg et al. | |
| 2004/0001888 A1 | 1/2004 | Jin | |
| 2004/0013697 A1 | 1/2004 | Berndl et al. | |
| 2004/0013734 A1 | 1/2004 | Babcock et al. | |
| 2004/0014817 A1 | 1/2004 | Rosenberg et al. | |
| 2004/0029892 A1 | 2/2004 | Rosenberg et al. | |
| 2004/0062802 A1 | 4/2004 | Hermelin | |
| 2004/0091529 A1 | 5/2004 | Edgren et al. | |
| 2004/0096499 A1 | 5/2004 | Vaya et al. | |
| 2004/0156905 A1 | 8/2004 | Babcock et al. | |
| 2004/0185170 A1 | 9/2004 | Chungi et al. | |
| 2004/0258752 A1 | 12/2004 | Paruthi et al. | |
| 2005/0003004 A1 | 1/2005 | Vehring et al. | |
| 2005/0008706 A1 | 1/2005 | Holm et al. | |
| 2005/0025791 A1 | 2/2005 | Remenar et al. | |
| 2005/0031691 A1 | 2/2005 | McGurk et al. | |
| 2005/0048112 A1 | 3/2005 | Breitenbach et al. | |
| 2005/0079138 A1 | 4/2005 | Chickering, III et al. | |
| 2005/0084529 A1 | 4/2005 | Rosenberg et al. | |
| 2005/0100586 A1 | 5/2005 | Sournac et al. | |
| 2005/0143404 A1 | 6/2005 | Rosenberg et al. | |
| 2006/0257470 A1 | 11/2006 | Rosenberg et al. | |
| 2007/0249692 A1 * | 10/2007 | Fort et al. | 514/365 |

FOREIGN PATENT DOCUMENTS

| | | |
|---|---|---|
| CA | 2 352 874 | 6/2000 |
| CA | 2 367 020 | 9/2000 |
| CA | 2 368 625 | 10/2000 |
| CA | 2 374 931 | 1/2001 |
| CA | 2 479 749 | 10/2003 |
| CA | 2501245 | 4/2004 |
| CA | 2 568 378 | 12/2005 |
| EP | 0 414 422 | 2/1991 |
| EP | 0852140 | 7/1998 |
| EP | 0 864 324 | 9/1998 |
| EP | 0 864 326 | 9/1998 |
| EP | 0 988 106 | 3/2000 |
| EP | 0 732 923 | 12/2001 |
| EP | 0 942 721 | 1/2003 |
| EP | 0 852 140 | 12/2003 |
| EP | 1227797 | 1/2005 |
| EP | 1175205 | 6/2006 |
| GB | 2 053 681 | 2/1981 |
| WO | 90/06115 | 6/1990 |
| WO | 95/07696 | 3/1995 |
| WO | 95/09614 | 4/1995 |
| WO | 95/22319 | 8/1995 |
| WO | 96/23499 * | 8/1996 |
| WO | 97/06781 | 2/1997 |
| WO | 9706781 | 2/1997 |
| WO | 97/46222 | 12/1997 |
| WO | 9746222 | 12/1997 |
| WO | 98/22106 | 5/1998 |
| WO | 98/24430 | 6/1998 |
| WO | 00/57854 | 10/2000 |
| WO | 00/74677 | 12/2000 |
| WO | 01/00175 | 1/2001 |
| WO | 01/22938 | 4/2001 |
| WO | 01/23362 | 4/2001 |
| WO | 01/34118 | 5/2001 |
| WO | 01/34119 | 5/2001 |
| WO | WO2001034118 | 5/2001 |

| | | |
|---|---|---|
| WO | 01/52821 | 7/2001 |
| WO | 01/91727 | 12/2001 |
| WO | 02/20057 | 3/2002 |
| WO | 02/092595 | 11/2002 |
| WO | 02/096395 | 12/2002 |
| WO | 03/080120 | 10/2003 |
| WO | WO2004032903 | 4/2004 |
| WO | 2004/039349 | 5/2004 |
| WO | 2004/050068 | 6/2004 |
| WO | 2004/054568 | 7/2004 |
| WO | 2005/004836 | 1/2005 |
| WO | 2005/007139 | 1/2005 |
| WO | WO2005/039551 | 5/2005 |

OTHER PUBLICATIONS

J. L. Ford, "The Current Status of Solid Dispersions", Pharm Acta Helv. 61. Nr. 3, (1986) 69-88.

B. J. Aungst, et al., "Improved Oral Bioavailability of an HIV Protease Inhibitor Using Celucire 44/14 and Labrasol Vehicles", B.T. Gattetosse, 87 (1994), 49-54.

B. J. Aungst, et al., "Amphiphilic Vehicles Improve the Oral Bioavailability of a Poorly Soluble HIV Protease Inhibitor at High Doses", International Journal of Pharmaceutics, 156 (1997) 79-88.

U.S. Appl. No. 09/438,994, filed Nov. 12, 1999, Fort et al.

Devalina Law et al., Physicochemical Considerations in the Preparation of Amorphous Ritonavir-Poly(ethyleneglycol) 6000 Soild Dispersions, J. Pharm. Sciences, (Aug. 2001), 1015-1025, 90(8).

U.S. Appl. No. 11/691,819, filed Mar. 27, 2007, Fort et al.

Aungst, B.J., et al., "Improved Oral Bioabilability of an HIV Protease Inhibitor Using Gelucire 44/14 and Labrasol Vehicles", *B.T. Gattefosse*, 87:49-54 (1994).

Awni, W., et al., "Significantly Reduced Food Effect and Pharmacokinetic Variability with a Novel Lopinavir/Ritonavir Tablet Formulation", *third IAS Conf. On HIV Pathogenesis and Treatment*, (2005).

BASF Fine Chemicals, "ExAct Excipients & Actives for Pharma", BASF, 2:1-16 (1999).

Bouma, M.G., et al., "Novel Therapeutic Delivery Systems", *J. of Contr. Rel.*, 87:199-308 (2003).

Breitenbach, J., "Melt Extrusion Can Bring New Benefits to HIV Therapy: The Example of Kaletra (R) Tablets", *Amer. :J. of Drug Deliv.*, 4(2):61-64 (2006).

Breitenbach, J., "Melt extrusion: from process to drug delivery technology", *Eur. J. of Pharm. & Biopharm.*, 54:107-117 (2002).

Chiou, W.L. & Riegelman, S., "Pharmaceutical Applications of Solid Dispersion Systems", *J. of Pharm. Sci.*, 60(9):1281-1301 (1971).

Corrigan, I.I. & Healy, A.M., "Surfactants in Pharmaceutical Products and Systems", *Encycl. Of Pharm. Tech.*, 2639-2653 (2002).

Ford, J.L., "The Current Status of Solid Dispersions", *Pharm. Acta Helv.*, 61(3):69-88 (1986).

Forster, A., et al., "Selection of excipients for melt extrusion with two poorly water-soluble drugs by solubility parameter calculation and thermal analysis", *Intn'l J. of Pharm.*, 226:147-161 (2001).

Hulsmann, S., et al., "Melt extrusion—an alternative method for enhancing the eissolution rate of 17β-estradiol hemihydrate", *Eur. J. of Pharm. & Biopharm.*, 49:237-242 (2000).

International Search Report & Written Opinion from PCT/US2004/027401 dated May 8, 2006.

Karanth, H., et al., "Industrially Feasible Alternative Approaches in the Manufacture of Solid Dispersions: A Technical Report", *AAPS PharmSciTech*, 7(4):Art. 87 (2006).

Law, D., et al., "Physicochemical Considerations in the Preparation of Amorphous Ritonavir-Poly(ethylene glycol) 8000 Solid Dispersions", *J. of Pharm. Sci.*, 90(8):1015-1025 (2001).

Law, D., et al., "Ritonavir-PEG 8000 Amorphous Solid Dispersions: In Vitro and in Vivo Evaluations", *J. of Pharm. Sci.*, 93(3):563-570 (2004).

Palmieri, G.F., et al., "Characterization and dissolution studies of PEG 4000/fenofibrate solid dispersions", *S.T.P. Pharma Sci.*, 6(3):188-194 (1996).

Physicians Desk Reference, online excert, PDR Electronic Library, not dated.

Physicians Desk Reference, online . . . Norvir, Fenofibrate, and Greiseosulvin, not dated.

Serajuddin, A.T.M., "Solid Dispersion of Poorly Water-Soluble Drugs: Early Promises, Subsequent Problems and Recent Breakthroughs", *J. of Pharm. Sci.*, 88(10):1058-1066 (1999).

U.S. Appl. No. 09/438,994, James J. Fort, et al., filed Nov. 12, 1999.

U.S. Appl. No. 11/691,819, James J. Fort, et al., filed Mar. 27, 2007.

U.S. Appl. No. 11/773,185 Joerge Rosenberg, et al., filed Jul. 3, 2007.

Zhu, T., et al., "New Tablet Formulation of Lopinavir/Ritonavir is Bioequivalent to the Capsule at a Dose 800/200 mg", *48th Int. Conf. On Antimic. Agents & Chem.*, (ICAAC), (2005).

* cited by examiner

SOLID DISPERSION PHARMACEUTICAL FORMULATIONS

This application claims the benefit of U.S. Provisional Application for Patent No. 60/165,018, filed Nov. 12, 1999.

TECHNICAL FIELD OF THE INVENTION

The instant invention relates to the fields of pharmaceutical and organic chemistry, and provides novel solid dispersion pharmaceutical formulations with enhanced bioavailability.

BACKGROUND OF THE INVENTION

One measure of the potential usefulness of an oral dosage form of a pharmaceutical agent is the bioavailability observed after oral administration of the dosage form. Various factors can affect the bioavailability of a drug when administered orally. These factors include aqueous solubility, drug absorption throughout the gastrointestinal tract, dosage strength, and first pass effect. Aqueous solubility is one of the most important of these factors. When a drug has poor aqueous solubility, attempts are often made to identify salts or other derivatives of the drug which have improved aqueous solubility. When a salt or other derivative of the drug is identified which has good aqueous solubility, it is generally accepted that an aqueous solution formulation of this salt or derivative will provide the optimum oral bioavailability. The bioavailability of the aqueous oral solution formulation of a drug is then generally used as the standard or ideal bioavailability against which other oral dosage forms are measured.

For a variety of reasons, including patient compliance and taste masking, a solid dosage form, such as a capsule or tablet, is usually preferred over a liquid dosage form. However, oral solid dosage forms of a drug generally provide a lower bioavailability than oral solutions of the drug. One goal of the development of a suitable solid dosage form is to obtain a bioavailability of the drug that is as close as possible to the ideal bioavailability demonstrated by the oral aqueous solution formulation of the drug.

An alternative dosage form is a solid dispersion. The term solid dispersion refers to the dispersion of one or more active ingredients in an inert carrier or matrix at solid state prepared by the melting (or fusion), solvent, or melting-solvent methods. (Chiou and Riegelman, *Journal of Pharmaceutical Sciences*, 60, 1281 (1971)). The dispersion of a drug or drugs in a solid diluent by mechanical mixing is not included in this category. Solid dispersions may also be called solid-state dispersions.

Retroviral protease inhibiting compounds are useful for inhibiting HIV proteases in vitro and in vivo, and are useful for inhibiting HIV (human immunodeficiency virus) infections and for treating AIDS (acquired immunodeficiency syndrome). HIV protease inhibiting compounds typically are characterized by having poor oral bioavailability. Examples of HIV protease inhibiting compounds include (2S,3S,5S)-5-(N—(N—((N-methyl-N-((2-isopropyl-4-thiazolyl)methyl)amino)carbonyl)-L-valinyl)amino)-2-(N-((5-thiazolyl)methoxy-carbonyl)-amino)-1,6-diphenyl-3-hydroxyhexane (ritonavir);

(2S,3S,5S)-2-(2,6-Dimethylphenoxyacetyl)amino-3-hydroxy-5-[2S-(1-tetrahydro-pyrimid-2-onyl)-3-methyl butanoyl]-amino-1,6-diphenylhexane (ABT-378);

N-(2(R)-hydroxy-1 (S)-indanyl)-2(R)-phenylmethyl-4(S)-hydroxy-5-(1-(4-(3-pyridylmethyl)-2(S)—N'-(t-butylcarboxamido)-piperazinyl))-pentaneamide(indinavir);

N-tert-butyl-decahydro-2-[2(R)-hydroxy-4-phenyl-3(S)-[[N-(2-quinolylcarbonyl)-L-asparaginyl]amino]butyl]-(4aS,8aS)-isoquinoline-3(S)-carboxamide(saquinavir);

5(S)-Boc-amino-4(S)-hydroxy-6-phenyl-2(R)-phenylmethylhexanoyl-(L)-Val-(L)-Phe-morpholin-4-ylamide;

1-Naphthoxyacetyl-beta-methylthio-Ala-(2S,3S)-3-amino-2-hydroxy-4-butanoyl 1,3-thiazolidine-4-t-butylamide;

5-isoquinolinoxyacetyl-beta-methylthio-Ala-(2S,3S)-3-amino-2-hydroxy-4-butanoyl-1,3-thiazolidine-4-t-butylamide;

[1S-[1R—(R—),2S*]—$N^1$[3-[[[(1,1-dimethylethyl)amino] carbonyl](2-methylpropyl)amino]-2-hydroxy-1-(phenylmethyl)propyl]-2-[(2-quinolinylcarbonyl)amino]-butanediamide;

VX-478; DMP-323; DMP-450; AG1343 (nelfinavir); BMS 186,318; SC-55389a; BILA 1096 BS; and U-140690, or combinations thereof.

While some drugs would be expected to have good solubility in organic solvents, it would not necessarily follow that oral administration of such a solution would give good bioavailability for the drug.

Polyethylene glycol (PEG) solid dispersion formulations are generally known to improve the dissolution and bioavailability of many compounds. However, Aungst et al. has recently demonstrated that this was unable to improve the bioavailability of an HIV protease inhibitor with a cyclic urea structural backbone, called DMP 323 (Aungst et al., *International Journal of Pharmaceutics*, 156, 79 (1997)).

Thus, it would be a significant contribution to the art to provide a solid dispersion pharmaceutical formulation of a retroviral protease inhibitor which is more stable and has enhanced bioavailability.

SUMMARY OF THE INVENTION

The instant invention provides a stable solid dispersion comprising a retroviral protease inhibitor and PEG having improved bioavailability.

Also provided by the instant invention is a pharmaceutical composition comprising a stable solid dispersion as described above with a pharmaceutically acceptable carrier, diluent, or excipient.

Additionally provided by the instant invention is a method for preparing a stable solid dispersion as described above.

The instant invention still further provides a method of treating an HIV infection comprising administering an effective amount of a stable solid dispersion as described above to a mammal in need of such treatment.

DETAILED DESCRIPTION OF THE INVENTION

Figure 1:
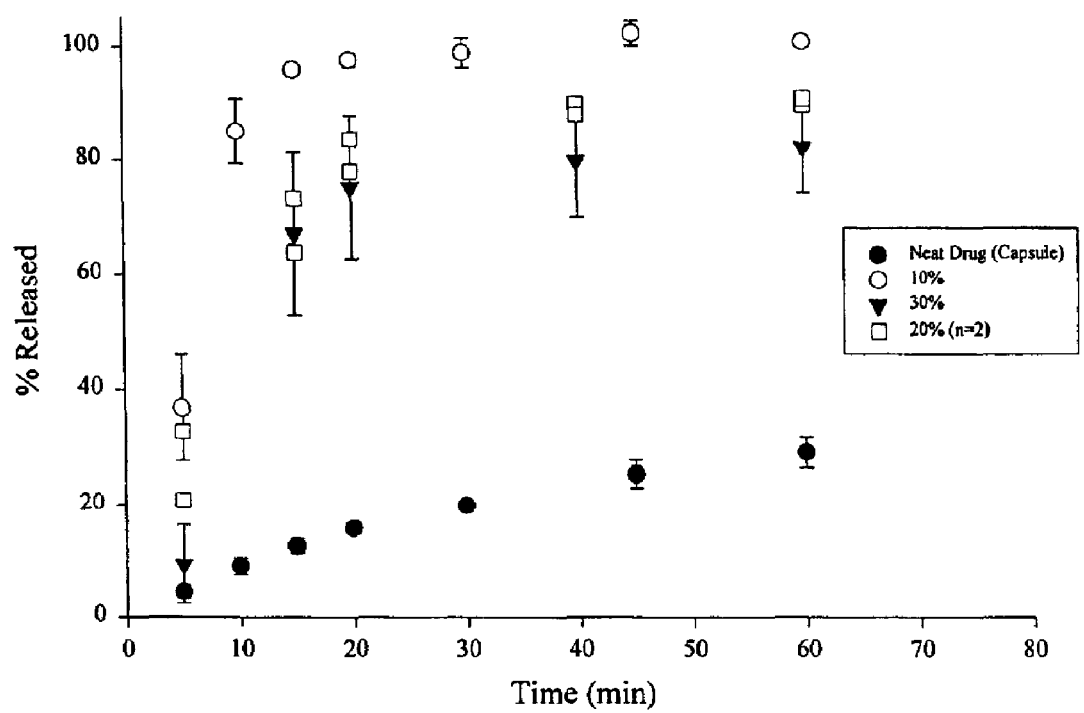
FIG. 1 illustrates the dispersion of amorphous ABT-538 in PEG 8000.

This invention pertains to the preparation of solid dispersion systems for protease inhibitors with improved dissolution and oral bioavailability.

A solid (molecular) dispersion comprising an HIV protease inhibiting compound may be prepared by dissolving or dispersing the HIV protease inhibiting compound in a sufficient amount of an organic solvent followed by dispersion into a suitable water soluble carrier. Suitable organic solvents include pharmaceutically acceptable solvents such as methanol, ethanol, or other organic solvents in which the protease inhibitor is soluble. Suitable water soluble carriers include polymers such as polyethylene glycol (PEG), pluronics, pentaeythritol, pentaeythritol tetraacetate, polyoxyethylene stearates, poly-ε-caprolactone, and the like.

The organic solvent (preferably ethanol) may then be evaporated away, leaving the drug dispersed/dissolved in the molten matrix, which is then cooled. The solid matrix has the compound finely dispersed (molecular dispersion) in such a way that dissolution of the drug is maximized, thus improving the bioavailability of a drug exhibiting dissolution rate limited absorption. Ease of manufacturing is also an attribute to this type of formulation. Once the organic solvent is evaporated to yield a solid mass, the mass may be ground, sized, and optionally formulated into an appropriate delivery system. Thus, by improving the dissolution of a poorly water soluble drug, the drug in a suitable carrier may be filled into a gelatin capsule as a solid, or the matrix may potentially be compressed into a tablet.

The delivery system of the present invention results in increased solubility and bioavailability, and improved dissolution rate of the HIV protease inhibiting compound.

Other pharmaceutically-acceptable excipients may be added to the formulation prior to forming the desired final product. Suitable excipients include lactose, starch, magnesium stearate, or other pharmaceutically-acceptable fillers, diluents, lubricants, disintegrants, and the like, that might be needed to prepare a capsule or tablet.

The resulting composition comprising the HIV protease inhibiting compound may be dosed directly for oral administration, diluted into an appropriate vehicle for oral administration, filled into capsules, or made into tablets for oral administration, or delivered by some other means obvious to those skilled in the art. The composition can be used to improve the oral bioavailability and solubility of said HIV protease inhibiting compound.

Total daily dosing of HIV protease inhibitors may be administered to a human in single or divided doses in amounts, for example, from 0.001 to 1000 mg/kg body weight daily, but more usually 0.1 to 50 mg/kg body weight daily. Dosage unit compositions may contain such amounts of submultiples thereof to make up the daily dose. It will be understood, however, that the specific dose level for any particular patient will depend upon a variety of factors including the age, body weight, general health, sex, diet, time of administration, rate of excretion, drugs administered in combination and the severity of the particular disease undergoing therapy.

ABT-538 (ritonavir) was preferably used as the HIV protease inhibitor in the instant invention. Additionally, two other protease inhibitors, ABT-378 and nelfinavir mesylate, were tested in solid dispersions to demonstrate the improved dissolution which can be achieved with this system.

One aspect of the instant invention provides a solid dispersion of a compound of formula I

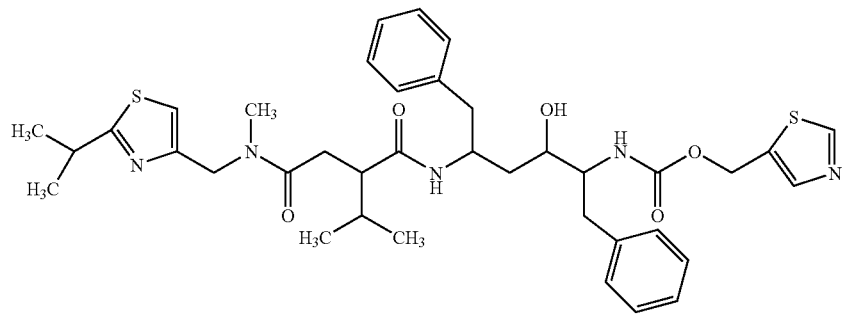

I

A compound of formula I is an HIV protease inhibitor marketed by Abbott Laboratories under the tradename Norvir®, with the common name ritonavir [(2S,3S,5S)-5-(N—(N—((N-methyl-N-((2-isopropyl-4-thiazolyl)-methyl) amino)carbonyl)-L-valinyl)amino)-2-(N-((5-thiazolyl) methoxy-carbonyl)-amino)-1,6-diphenyl-3-hydroxyhexane]. This and other compounds as well as methods for preparing the same are disclosed in U.S. Pat. Nos. 5,648,497 and 5,541,206, the disclosures of which are herein incorporated by reference.

Additional HIV protease inhibitors which may be formulated into a solid dispersion include compounds of formula II

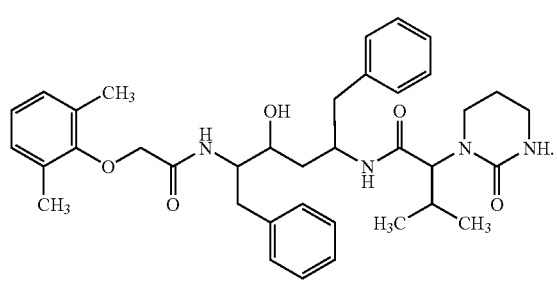

II

A compound of formula II is known as ABT-378 ((2S,3S, 5S)-2-(2,6-dimethylphenoxyacetyl)-amino-3-hydroxy-5-(2S—(1-tetrahydropyrimid-2-onyl)-3-methyl-butanoyl) amino-1,6-diphenylhexane). This and other compounds, as well as methods for preparing same, are identified in U.S. Pat. No. 5,914,332, the disclosure of which is herein incorporated by reference.

A compound of formula III provided hereinbelow is known as nelfinavir mesylate (marketed under the tradename Viracept® by Agouron Pharmaceuticals, Inc. in La Jolla, Calif.), and is another HIV protease inhibitor which may be formulated into a solid dispersion.

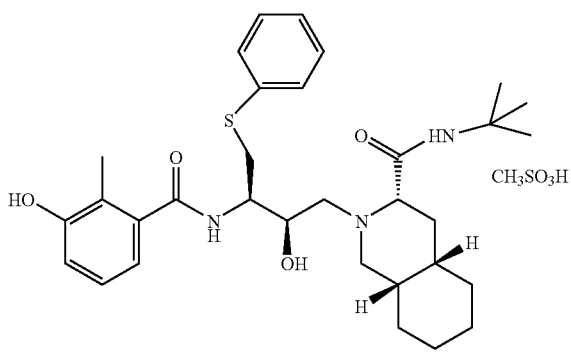

III

The following Examples are provided to further illustrate the present invention.

EXAMPLES

Example 1

Dispersion Preparations

A. Ritonavir (ABT-538) Dispersion Preparation:

The samples were prepared by dissolving ABT-538 in a small volume of 200 proof ethanol in a 250 ml round bottom flask. The flask was vortexed and then placed in a water bath maintained at 75° C. The PEG 8000 was added to the hot alcohol solution with continual swirling until the PEG melted. The flask was then attached to a rotary evaporator, immersed in the water bath (75° C.) under vacuum for 15 minutes to remove the ethanol. After the majority of ethanol had evaporated, the flask was immersed in an ice bath for 15 minutes. The contents of the flask were then vacuum dried at room temperature for 6 hours. The solid was transferred to a crystallization dish and placed under vacuum overnight to remove residual ethanol. The material was then ground and sifted. Particles ranging in size from to 420 μm were used for further studies. The drug used for these dispersions were 10, 20 and 300 w/w.

B. ABT-378 Dispersion Preparation:

A 10% dispersion was prepared using an alcoholic solution of ABT-378 (ca. 0.1 g/ml) by the same method as described in section A above.

C. Nelfinavir mesylate Dispersion Preparation:

Nelfinavir mesylate is available from Agouron Pharmaceuticals, Inc. under the tradename Virucept®.

A 10% dispersion was prepared using an alcoholic solution of nelfinavir (ca. 0.035 g/ml) by the same method as described in section A above.

The potency values of all the dispersions as well as the dissolution sample concentrations were determined via HPLC.

D. Results:

The in vitro dissolution data of the ABT-538 dispersions compared with ABT-538 in 0.1N HCl (shown in FIG. 1, n=3±SD unless otherwise indicated) show that the dispersions markedly improved the dissolution rate of the drug. Drug loading decreases the rate of drug release in a rank order. A bioavailability study was conducted in dogs with the above ABT-538 dispersions to elicit the drug load effects in vivo. Eight beagle dogs, obtained from Marshall Research Animals (North Rose, N.Y.), were utilized in this study. The animals were fasted overnight prior to dosing in each period but water was allowed ad libitum. Approximately 30 minutes prior to dosing, each dog received a 100 μg/kg subcutaneous dose of histamine. Capsules containing 5 mg/kg of 10, 20 and 30% solid dispersion (formulations A, B and C, respectively) were tested against crystalline drug as a reference in a four-way crossover study.

Each dog received the dose followed by approximately 10 ml of water. A washout period of approximately 1 week was used to separate each dosing period. The plasma samples were analyzed by a method reported by Marsh et al. (Marsh, K. C., Eiden, E. and McDonald, E. Determination of Ritonavir, a new HIV Protease Inhibitor, in Biological Samples Using Reversed-Phase High-Performance Liquid Chromatography. *J. Chromatography B*. 704 (1997) 307-313.)

Figure 2:
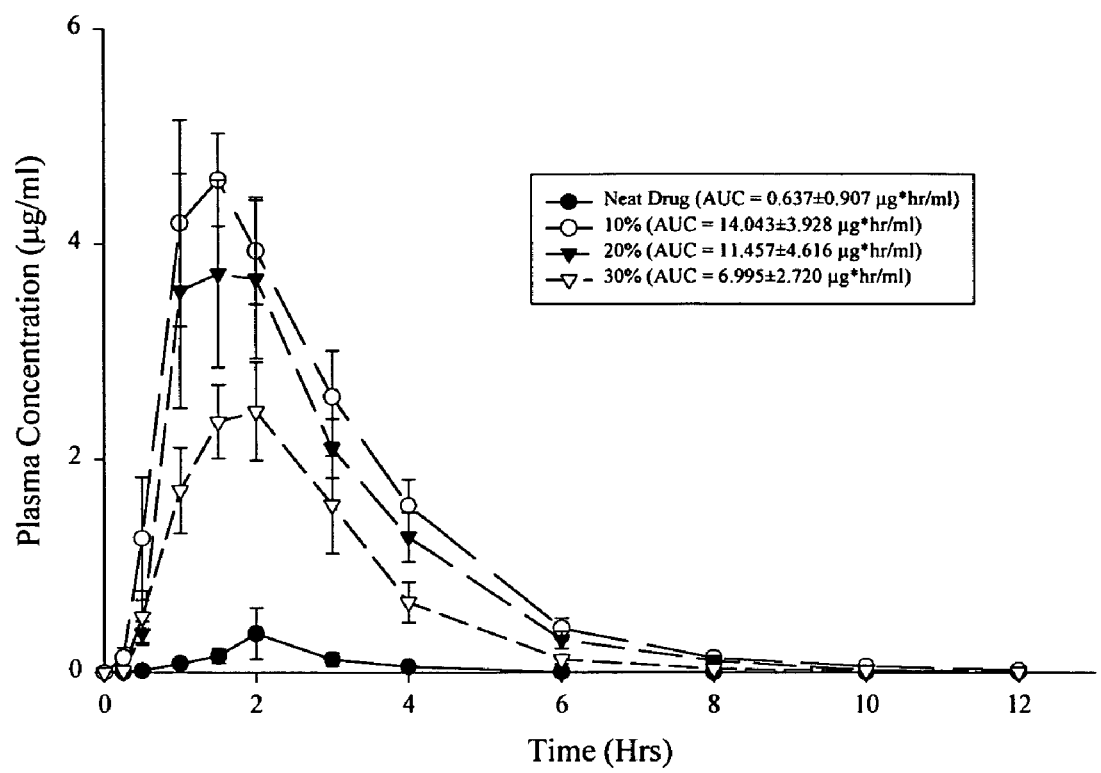
FIG. 2 illustrates the bioavailability of a dispersion of amorphous ABT-538 in PEG 8000.
Figure 3:
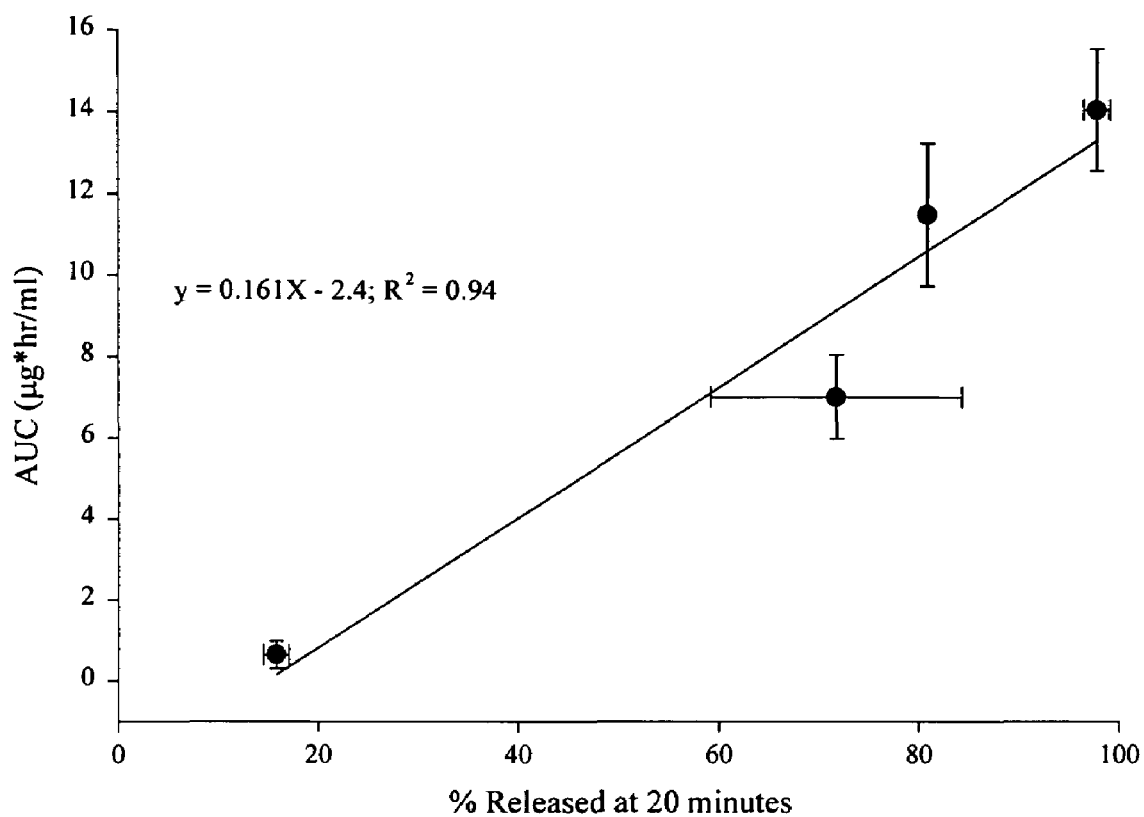
FIG. 3 illustrates the in vivo-in vitro correlation of ABT-538.

The results of the study are shown in FIG. 2. The results show that the solid dispersions improve absorption compared to the reference. An in vitro—in vivo correlation was established. A plot of the AUC versus the amount dissolved in 20 min, shown in FIG. 3, is a straight line, indicating excellent correlation.

Figure 4:
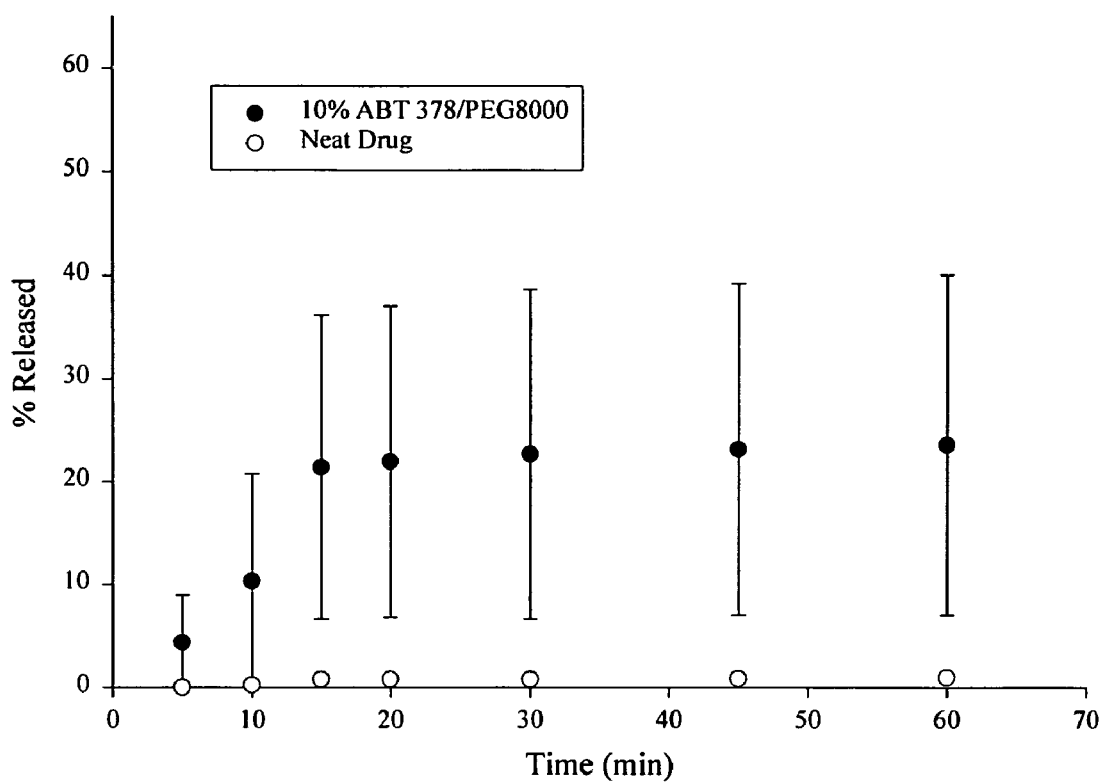
FIG. 4 illustrates the dissolution of ABT-378.

The dissolution properties of the two additional protease inhibitors (ABT-378 and nelfinavir mesylate) were also determined. The in vitro dissolution data (FIG. 4) of the ABT-378 dispersion compared with reference clearly shows that the preparation of a dispersion markedly improves dissolution rate of the drug. The variability in the release rate from the dispersion is due to the fact that the preparation of these dispersions had not been optimized to completely overcome the wetting problem of the drug. Despite this, the improvements observed are significant [95% confidence intervals shown].

Figure 5:
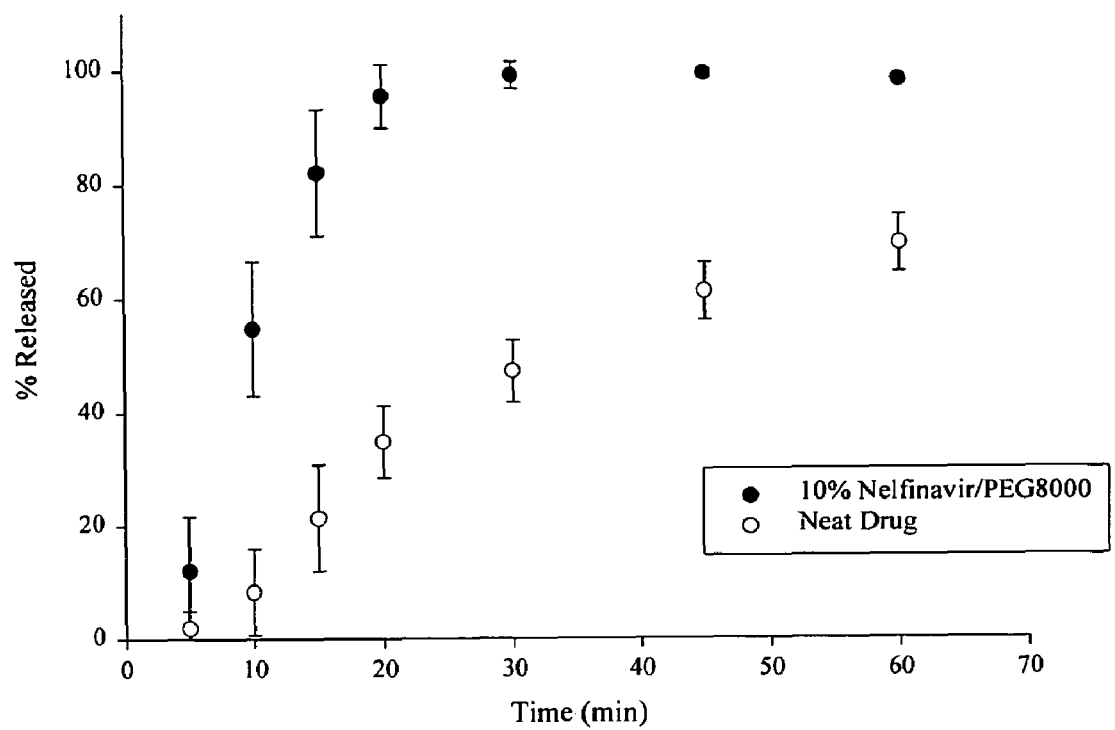
FIG. 5 illustrates the dissolution of nelfinavir.

The nelfinavir mesylate solid dispersion also exhibits an improved in vitro dissolution rate compared to the neat drug (FIG. 5).

E. Conclusions:

Solid dispersions of HIV protease inhibitors (for example, ABT-538 (ritonavir), ABT-378, and nelfinavir mesylate) markedly improve the dissolution rate of these drugs. This improvement of dissolution rate is reflected in the improvement of bioavailability. An excellent in vivo—in vitro correlation established for the dispersions suggests that the in vitro dissolution reflects in vivo bioavailability for these systems.

Example 2

Stability of Dispersion in Molten PEG 8000

The stability of the dispersion of ABT-538 in PEG 8000 in the molten state at 70° C. was examined. Individual approximately 5 mg quantities of the dispersion (aged for 6 weeks at room temperature) were placed in 4 ml glass vials. These vials, with the exception of the initial time point, were placed in a 70° C. oven which was sampled at pre-determined intervals, chilled in ice water and placed in the freezer until HPLC analysis. After all samples were collected, they were analyzed for ABT-538 content by HPLC. The HPLC system consisted of a Hitachi AS 4000 autosampler, SP 8800 ternary pump, Applied Biosystems 783 detector, and PE Nelson Data acquisition system. Other chromatographic details included a Regis Little Champ 5 cm C-18 column, a mobile phase consisting of an aqueous solution of 0.1% trifluoroacetic acid in 10 mM aqueous tetramethyl ammonium perchlorate (TMAP)/acetonitrile/methanol (55/40/5). The flow rate was 1 ml/minute, the wavelength of detection was 205 nm, and the injection volume was 100 µl. Standard curves of peak area of ABT-538 vs. concentration in the range of interest were compared with experimentally obtained area counts.

Example 3

Additional Protocol for Oral Bioavailability Studies

Dogs (beagle dogs, mixed sexes, weighing 7-14 kg) are fasted overnight prior to dosing, but are permitted water ad libitum. Each dog receives a 100 µg/kg subcutaneous dose of histamine approximately 30 minutes prior to dosing. Each dog receives a single solid dosage form corresponding to a 5 mg/kg dose of the drug. The dose is followed by approximately 10 milliliters of water. Blood samples are obtained from each animal prior to dosing and at 0.25, 0.5, 1.0, 1.5, 2, 3, 4, 6, 8, 10 and 12 hours after drug administration. The plasma is separated from the red cells by centrifugation and frozen (−30° C.) until analysis. The concentrations of parent drug is determined by reverse phase HPLC with low wavelength UV detection following liquid-liquid extraction of the plasma samples. The parent drug area under the curve is calculated by the trapezoidal method over the time course of the study. The absolute bioavailability of each test composition is calculated by comparing the area under the curve after oral dosing to that obtained from a single intravenous dose. Each capsule or capsule composition is evaluated in a group containing at least six dogs. The values reported are averages for each group of dogs.

What is claimed is:

1. A pharmaceutical composition comprising ritonavir, wherein ritonavir in said composition is formulated as a solid dispersion of amorphous ritonavir in a matrix including a water soluble polymer.

2. A pharmaceutical composition of claim 1, comprising a gelatin capsule which encapsulates said solid dispersion.

3. A pharmaceutical composition of claim 1 which is a tablet comprising said solid dispersion.

4. The pharmaceutical composition of claim 1, wherein said water soluble polymer is PEG.

5. The pharmaceutical composition of claim 1, wherein said water soluble polymer is PEG 8000.

6. The pharmaceutical composition of claim 1, wherein said solid dispersion further comprises (2S,3S,5S)-2-(2,6-dimethylphenoxyacetyl)amino-3-hydroxy-5-[2S-(1-tetrahydro-pyrimid-2-onyl)-3-methylbutanoyl]amino-1,6-diphenylhexane (ABT-378).

7. The pharmaceutical composition of claim 1, further comprising a pharmaceutically-acceptable filler, diluent, lubricant or disintegrant.

8. The pharmaceutical composition of claim 1, wherein said solid dispersion is ground and formulated into a delivery system.

9. A method of treating an HIV infection comprising administering a pharmaceutical composition of claim 1 to a mammal in need of such treatment.

10. A method of treating an HIV infection comprising administering the pharmaceutical composition of claim 6 to a mammal in need of such treatment.

* * * * *

UNITED STATES PATENT AND TRADEMARK OFFICE
CERTIFICATE OF CORRECTION

PATENT NO. : 7,364,752 B1  
APPLICATION NO. : 09/709829  
DATED : April 29, 2008  
INVENTOR(S) : Fort et al.

Page 1 of 1

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by (688) days Delete the phrase "by 688 days" and insert -- by 0 days --

Signed and Sealed this

Sixth Day of January, 2009

JON W. DUDAS  
*Director of the United States Patent and Trademark Office*

(12) INTER PARTES REEXAMINATION CERTIFICATE (1039th)
United States Patent
Fort et al.

(10) Number: US 7,364,752 C1
(45) Certificate Issued: Jan. 23, 2015

(54) SOLID DISPERSION PHARMACEUTICAL FORMULATIONS

(75) Inventors: James J. Fort, Midlothian, VA (US); Steven L. Krill, Chatham, NJ (US); Devalina Law, Libertyville, IL (US); Yihong Qiu, Gurnee, IL (US); William R. Porter, Vernon Hills, IL (US); Eric A. Schmitt, Libertyville, IL (US)

(73) Assignee: Abbott Laboratories, Abbott Park, IL (US)

Reexamination Request:
No. 95/002,020, Jun. 15, 2012

Reexamination Certificate for:
Patent No.: 7,364,752
Issued: Apr. 29, 2008
Appl. No.: 09/709,829
Filed: Nov. 10, 2000

Certificate of Correction issued Jan. 6, 2009

Related U.S. Application Data

(60) Provisional application No. 60/165,018, filed on Nov. 12, 1999.

(51) Int. Cl.
*A61K 8/72* (2006.01)
*A61K 31/425* (2006.01)
*A61K 31/505* (2006.01)
*A61K 9/20* (2006.01)
*A61K 9/48* (2006.01)
*A61K 9/16* (2006.01)

(52) U.S. Cl.
CPC ............. *A61K 9/1641* (2013.01); *A61K 31/505* (2013.01); *A61K 31/425* (2013.01); *A61K 9/167* (2013.01); *A61K 9/2072* (2013.01); *Y10S 514/937* (2013.01)
USPC ........... 424/455; 424/464; 424/484; 424/486; 514/274; 514/772; 514/772.3; 514/937

(58) Field of Classification Search
None
See application file for complete search history.

(56) References Cited

To view the complete listing of prior art documents cited during the proceeding for Reexamination Control Number 95/002,020, please refer to the USPTO's public Patent Application Information Retrieval (PAIR) system under the Display References tab.

*Primary Examiner* — Evelyn Huang

(57) ABSTRACT

A pharmaceutical composition is disclosed which comprises a solid dispersion of an HIV protease inhibitor in a water soluble carrier, such as PEG, having enhanced bioavailability and improved dissolution properties. The solid dispersion may optionally be encapsulated in hard gelatin capsules, compressed into a tablet, or may be granulated with a pharmaceutically acceptable granulating agent. Also disclosed are methods of making said solid dispersion and methods of treating an HIV infection employing said solid dispersion.

INTER PARTES REEXAMINATION CERTIFICATE ISSUED UNDER 35 U.S.C. 316

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 8 is confirmed.

Claims 1-7, 9 and 10 are cancelled.

New claims 11-38 are added and determined to be patentable.

*11. The pharmaceutical composition of claim 1, wherein said solid dispersion is a ground solid dispersion.*

*12. The pharmaceutical composition of claim 2, wherein said solid dispersion is a ground solid dispersion.*

*13. The pharmaceutical composition of claim 3, wherein said solid dispersion is a ground solid dispersion.*

*14. The pharmaceutical composition of claim 4, wherein said solid dispersion is a ground solid dispersion.*

*15. The pharmaceutical composition of claim 5, wherein said solid dispersion is a ground solid dispersion.*

*16. The pharmaceutical composition of claim 6, wherein said solid dispersion is a ground solid dispersion.*

*17. The pharmaceutical composition of claim 7, wherein said solid dispersion is a ground solid dispersion.*

*18. The method of treating an HIV infection of claim 9, wherein said solid dispersion is a ground solid dispersion.*

*19. The method of treating an HIV infection of claim 10, wherein said solid dispersion is a ground solid dispersion.*

*20. The pharmaceutical composition of claim 1, wherein said solid dispersion is ground from a solid mass.*

*21. The pharmaceutical composition of claim 2, wherein said solid dispersion is ground from a solid mass.*

*22. The pharmaceutical composition of claim 3, wherein said solid dispersion is ground from a solid mass.*

*23. The pharmaceutical composition of claim 4, wherein said solid dispersion is ground from a solid mass.*

*24. The pharmaceutical composition of claim 5, wherein said solid dispersion is ground from a solid mass.*

*25. The pharmaceutical composition of claim 6, wherein said solid dispersion is ground from a solid mass.*

*26. The pharmaceutical composition of claim 7, wherein said solid dispersion is ground from a solid mass.*

*27. The method of treating an HIV infection of claim 9, wherein said solid dispersion is ground from a solid mass.*

*28. The method of treating an HIV infection of claim 10, wherein said solid dispersion is ground from a solid mass.*

*29. The pharmaceutical composition of claim 1, wherein said solid dispersion is prepared through cooling a molten matrix comprising ritonavir and said water-soluble polymer.*

*30. The pharmaceutical composition of claim 2, wherein said solid dispersion is prepared through cooling a molten matrix comprising ritonavir and said water-soluble polymer.*

*31. The pharmaceutical composition of claim 3, wherein said solid dispersion is prepared through cooling a molten matrix comprising ritonavir and said water-soluble polymer.*

*32. The pharmaceutical composition of claim 4, wherein said solid dispersion is prepared through cooling a molten matrix comprising ritonavir and said water-soluble polymer.*

*33. The pharmaceutical composition of claim 5, wherein said solid dispersion is prepared through cooling a molten matrix comprising ritonavir and said water-soluble polymer.*

*34. The pharmaceutical composition of claim 6, wherein said solid dispersion is prepared through cooling a molten matrix comprising ritonavir and said water-soluble polymer.*

*35. The pharmaceutical composition of claim 7, wherein said solid dispersion is prepared through cooling a molten matrix comprising ritonavir and said water-soluble polymer.*

*36. The pharmaceutical composition of claim 8, wherein said solid dispersion is prepared through cooling a molten matrix comprising ritonavir and said water-soluble polymer.*

*37. The method of treating an HIV infection of claim 9, wherein said solid dispersion is prepared through cooling a molten matrix comprising ritonavir and said water-soluble polymer.*

*38. The method of treating an HIV infection of claim 10, wherein said solid dispersion is prepared through cooling a molten matrix comprising ritonavir and said water-soluble polymer.*

\* \* \* \* \*